(12) United States Patent
Woo et al.

(10) Patent No.: US 10,473,562 B2
(45) Date of Patent: Nov. 12, 2019

(54) CORRUGATED-TUBE CONSTANT-PRESSURE CYLINDER APPARATUS HAVING NO MICROLEAKAGE AND METHOD FOR USING SAME

(71) Applicant: Korea Research Institute of Standards and Science, Yuseong-gu, Daejeon (KR)

(72) Inventors: Jin Choon Woo, Daejeon (KR); Yong Doo Kim, Daejeon (KR); Hyeon Gil Bae, Daejeon (KR); Nam Goo Gang, Daejeon (KR)

(73) Assignee: Korea Research Institute of Standards and Science, Daejeon (KR)

( * ) Notice: Subject to any disclaimer, the term of this patent is extended or adjusted under 35 U.S.C. 154(b) by 289 days.

(21) Appl. No.: 15/524,425

(22) PCT Filed: Jun. 4, 2015

(86) PCT No.: PCT/KR2015/005619
§ 371 (c)(1),
(2) Date: May 4, 2017

(87) PCT Pub. No.: WO2016/175371
PCT Pub. Date: Nov. 3, 2016

(65) Prior Publication Data
US 2018/0283994 A1 Oct. 4, 2018

(30) Foreign Application Priority Data
Apr. 25, 2015 (KR) .................. 10-2015-0058477

(51) Int. Cl.
*G01N 1/14* (2006.01)
*F16J 3/06* (2006.01)
(Continued)

(52) U.S. Cl.
CPC .............. *G01N 1/14* (2013.01); *B01L 3/508* (2013.01); *F16J 3/06* (2013.01); *G01N 1/00* (2013.01);
(Continued)

(58) Field of Classification Search
CPC ......... B01L 2300/0832; B01L 2300/14; B01L 3/508; G01N 1/00; G01N 1/14;
(Continued)

(56) References Cited

U.S. PATENT DOCUMENTS 4,686,851 A * 8/1987 Holm .................. G01M 3/3263
73/49.2
4,862,754 A * 9/1989 Nimberger ............... G01N 1/14
73/864.62

(Continued)

FOREIGN PATENT DOCUMENTS

| JP | 2537215 Y | 3/1997 |
|---|---|---|
| KR | 10-2015-0031015 | 3/2015 |
| WO | 2014-088278 | 6/2014 |

OTHER PUBLICATIONS

Search Report issued in International Application No. PCT/KR2015/005619, dated Jan. 20, 2016, 4 pages.

*Primary Examiner* — Francis C Gray
(74) *Attorney, Agent, or Firm* — Hamre, Schumann, Mueller & Larson, P.C.

(57) ABSTRACT

A corrugated constant pressure cylinder apparatus having no micro leaks and its method of use. The internal pressure of the corrugated cylinder (b10) is maintained at a constant pressure so as to allow for transport or storage in a state without micro leaks. The corrugated constant pressure cylinder apparatus is able to keep substances that exist in gaseous or liquid form at room temperature such as mixed refrigerant gases, volatile organic compounds (VOC), hydrocarbon mixtures-in liquid form, or is able to keep the (Continued)

pressure constant even if the internal volume changes due to the contents inside the cylinder.

6 Claims, 10 Drawing Sheets

(51) Int. Cl.
*B01L 3/00* (2006.01)
*G01N 1/00* (2006.01)
*G01N 1/22* (2006.01)
*G01N 1/10* (2006.01)

(52) U.S. Cl.
CPC . *B01L 2200/0689* (2013.01); *B01L 2200/142* (2013.01); *B01L 2200/18* (2013.01); *B01L 2300/0832* (2013.01); *B01L 2300/0861* (2013.01); *B01L 2300/10* (2013.01); *B01L 2300/123* (2013.01); *B01L 2300/14* (2013.01); *B01L 2400/0478* (2013.01); *B01L 2400/0487* (2013.01); *G01N 1/22* (2013.01); *G01N 2001/002* (2013.01); *G01N 2001/1062* (2013.01); *G01N 2001/1454* (2013.01)

(58) Field of Classification Search
CPC ............... G01N 1/22; G01N 2001/002; G01N 2001/1062; G01N 2001/1454; F16J 3/06
See application file for complete search history.

(56) References Cited

U.S. PATENT DOCUMENTS

| | | | |
|---|---|---|---|
| 4,922,764 A | 5/1990 | Welker | |
| 4,930,361 A * | 6/1990 | Nimberger | G01N 1/14 73/864.62 |
| 6,074,610 A * | 6/2000 | Huang | B01J 3/04 422/550 |
| 7,707,871 B2 * | 5/2010 | Lukens | G01M 3/229 73/40.7 |
| 9,274,021 B2 * | 3/2016 | Yamamoto | G01M 3/229 |
| 9,857,264 B2 * | 1/2018 | Watanabe | G01M 3/202 |
| 9,958,353 B2 * | 5/2018 | Daniels | G01M 3/2853 |
| 2017/0219425 A1 * | 8/2017 | Zorbach | G01J 1/0295 |

* cited by examiner

CORRUGATED-TUBE CONSTANT-PRESSURE CYLINDER APPARATUS HAVING NO MICROLEAKAGE AND METHOD FOR USING SAME

TECHNICAL FIELD

The present invention relates to a corrugated constant pressure cylinder apparatus having no micro leaks and its method of use, and more specifically, a corrugated constant pressure cylinder apparatus having no micro leaks and its method of use where the internal pressure of the cylinder is maintained at a constant pressure so as to allow for transport or storage in a state without micro leaks. Therefore, this invention relates to a corrugated constant pressure cylinder apparatus having no micro leaks and its method of use where mixed refrigerant gases, volatile organic compounds (VOC), hydrocarbon mixtures, and other such substances that exist in gaseous or liquid form at room temperature are kept in a cylinder that maintains a constant internal pressure to keep the contents in liquid form, or is able to keep the pressure constant even if the internal volume changes due to the contents inside the cylinder.

BACKGROUND ART

In order to accurately analyze the composition of a sample that consists of mixed refrigerant gases, volatile organic compounds (VOC), hydrocarbon mixtures, or other such substances that exist in gaseous or liquid form at room temperature, samples are taken at the sample collection site, transported to a laboratory, then placed into an analyzer that analyzes the sample.

It is a well known fact that a reliable analysis is obtained by continually injecting the liquid or gaseous sample into the analyzer at a constant pressure.

However, if the sample gas has a high vapor pressure like a hydrocarbon mixture so that even at the same pressure it is a mixture of liquid and gas, the sample being injected into the analyzer will be in an unstable state, making the results of the sample analysis unreliable.

Figure 11:
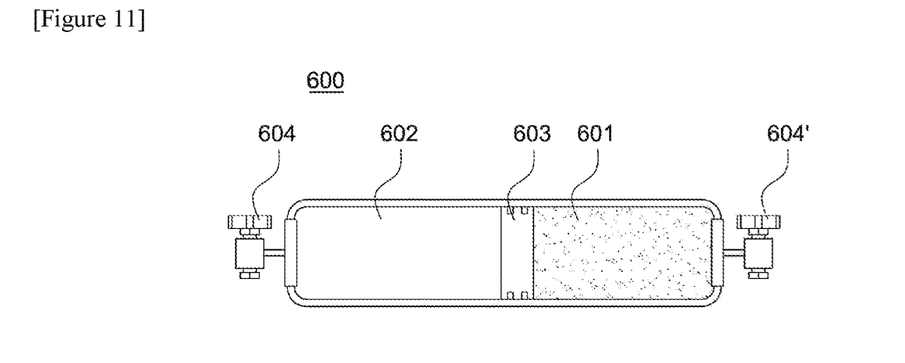
FIG. 11 is a conceptual diagram to explain the traditional piston-type constant pressure cylinder.
Figure 12:
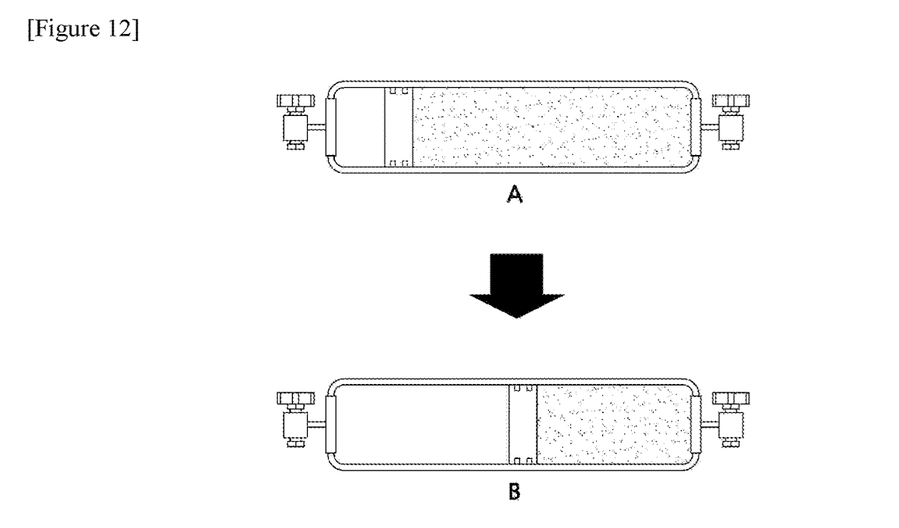
FIG. 12 is a conceptual diagram to explain the traditional piston-type constant pressure cylinder forming constant pressure after it contains the sample.

Traditionally, in order to maintain such aforementioned samples in a liquid state to be transported to the laboratory and analyzed, piston type constant pressure cylinders that use o-rings (Piston Type Constant Pressure Cylinder, 600), such as those depicted in the conceptual diagrams of FIG. 11 and FIG. 12, were utilized.

In other words, the aforementioned piston type constant pressure cylinder (600) is comprised of, as shown in FIG. 11, a sample chamber (601) that collects the sample; an inert gas chamber (602) into which an inert gas is injected so as to raise the pressure in the sample chamber (601) in accordance with the amount injected without affecting the sample; an o-ring piston (603) that forms a movable partition located in between the aforementioned sample chamber (601) and the inert gas chamber (602); opening/closing valves (604),(604') on the aforementioned sample chamber (601) and inert gas chamber (602); and connecting parts (605),(605') that connect the aforementioned sample chamber (601) and inert gas chamber (602) to the gas analysis system.

This aforementioned traditional piston type constant pressure cylinder (600) has a plurality of o-rings interposed on the edge of the end plate of the o-ring piston, and the o-ring piston (603) is coupled to allow for back and forth movement.

Furthermore one side of the cylinder divided by the aforementioned o-ring piston (603) forms the sample chamber (601), while the other side forms the inert gas chamber (602).

The aforementioned piston-type constant pressure cylinder (600) adjusts the pressure within the sample chamber (601) to the appropriate pressure by first closing the opening/closing valve (604) after filling the sample chamber (601) with the sample, then gradually increasing the amount of inert gas injected into the inert gas chamber (602).

In other words, when the sample within the aforementioned sample chamber (601) is in a liquid state, the injection of inert gas is stopped and the opening/closing valve (604) of the inert gas chamber (602) is closed.

Figure 13:
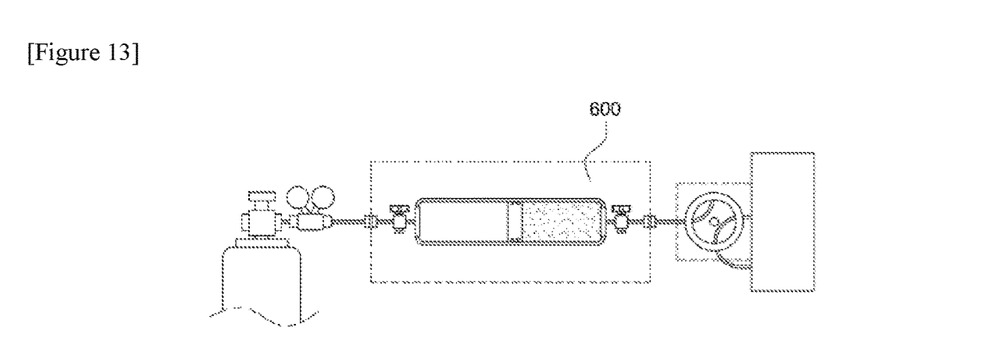
FIG. 13 is a diagram depicting one example of either the traditional piston-type constant pressure cylinder or the present invention's constant pressure cylinder that has no leaks that contains a sample that is being maintained at a constant pressure and has been installed on the analyzer.

At this point, as shown in FIG. 12, as the internal pressure of the inert gas chamber (602) goes up in response to the increase in the amount of inert gas injected, the o-ring piston (603) cannot overcome this pressure and is pushed towards the sample chamber (601) side, making the pressure inside the sample chamber (601) go up, and when the pressure within the sample chamber (601) is adjusted to the predetermined pressure, the opening/closing valve (604) of the inert gas chamber (602) is closed and the aforementioned piston-type constant pressure gas transport apparatus (600) is removed and transported to the laboratory after which, as shown in FIG. 13, it is installed onto the analyzer so as to analyze the composition of the sample.

However, while the aforementioned traditional piston-type constant pressure cylinder contributes somewhat to adjustments of the pressure within the sample chamber (601) to the appropriate pressure, as there are a plurality of o-rings interposed on the edge of the end plate of the o-ring piston and the piston is formed to allow for back and forth movement, leaks of trace amounts of gas form at the o-rings on the edge of the end plate of the piston, making it difficult to maintain constant pressure within the sample chamber or altering the composition of the sample, so as a result the sample within the sample chamber contains both liquid and gas, making the sample composition analysis unreliable.

In particular, when the sample contains trace amounts of a substance, the state of the sample being injected into the analyzer undergoes minute changes, making the composition analysis even more unreliable.

SUMMARY

The present invention relates to a corrugated constant pressure cylinder apparatus having no micro leaks and its method of use, and more specifically, a corrugated constant pressure cylinder apparatus having no micro leaks and its method of use where the internal pressure of the cylinder is maintained at a constant pressure so as to allow for transport or storage in a state without micro leaks. Therefore, this invention relates to a corrugated constant pressure cylinder apparatus having no micro leaks and its method of use where mixed refrigerant gases, volatile organic compounds (VOC), hydrocarbon mixtures, and other such substances that exist in gaseous or liquid form at room temperature are kept in a cylinder that maintains a constant internal pressure to keep the contents in liquid form, or is able to keep the pressure constant even if the internal volume changes due to the contents inside the cylinder.

In order to fulfill the aforementioned purpose, the corrugated constant pressure cylinder apparatus having no micro leaks of the present invention is characterized by being comprised of a fixed plate (100) comprised of a circular steel plate with a fixed thickness that has a sample inlet (101) in the middle that goes through the plate, and is coupled with the bottom portion of a cylinder (200) to form chamber (a) and; a cylinder (200) comprised of a steel tube open at the bottom section and closed at the upper section with the flared bottom section comprised of a flange (210) that has a plurality of fastening holes (211) going through it and is coupled with the aforementioned fixed plate (100) to form chamber (a) and; fastening bolts (300) and fastening nuts (300') that fasten together with bolts the aforementioned fixed plate's (100) inner side with the outer side of the flange (210) on the bottom section of the aforementioned cylinder (200) to form chamber (a) and; a pressure gauge (400) coupled to the coupling pipe (226) of the pressure gauge coupling hole (224) that checks the pressure within chamber (a) in order to control the amount of inert gas that is injected and; opening/closing valves (500) connected to the sample inlet (101) and the inert gas inlet (223) and; a sample chamber (b) inside the aforementioned chamber (a) that stores the collected sample and creates and maintains constant pressure.

In addition, the method of use for the corrugated constant pressure cylinder having no micro leaks of the present invention is characterized by collecting a fixed amount of the sample in sample chamber (b) then closing the opening/closing valve (500), opening the opening/closing valve (500') of the inert gas inlet (223) on the cylinder (200) then gradually injecting inert gas through the inert gas inlet (223), making the corrugated cylinder (b10) of sample chamber (b) adjust in accordance with the increase in inert gas injected into the aforementioned chamber (a) until the internal pressure of chamber (a) and the internal pressure of sample chamber (b) reach equilibrium at a predetermined pressure, at which time the opening/closing valve (500') of the inert gas inlet (223) is closed.

According to the corrugated constant pressure cylinder having no micro leaks and its method of use of the present invention as set forth above, a corrugated constant pressure cylinder having no micro leaks and its method of use is provided that removes the cause of gas leaks in the chamber and the sample chamber, allowing for the sample within the sample chamber to be maintained at a constant pressure to keep it in a liquid state during transport to the laboratory, which then allows it to be directly installed onto the analyzer to have the sample's composition be analyzed, resulting in reliable composition analysis results.

DETAILED EXPLANATION OF THE INVENTION

Technical Task

The present invention was devised to solve the aforementioned problems, and as such, offers a corrugated constant pressure cylinder having no micro leaks and its method of usage that allows for the pressure within the sample chamber of this invention, which is a corrugated constant pressure cylinder, to be maintained at a constant pressure, and by removing the cause of gas leaks in the chamber and the sample chamber, allow the sample within the sample chamber to be maintained at a constant pressure to keep it in a liquid state during transport to the laboratory and allow it to be directly installed onto the analyzer to have the sample's composition be analyzed, which allows for reliable sample composition analysis results.

Solution to the Technical Problem

In order to fulfill the aforementioned purpose, the corrugated constant pressure cylinder apparatus having no micro leaks of the present invention is characterized by being comprised of a fixed plate (100) comprised of a circular steel plate with a fixed thickness that has a sample inlet (101) in the middle that goes through the plate, and is coupled with the bottom portion of a cylinder (200) to form chamber (a) and; a cylinder (200) comprised of a steel tube open at the bottom section and closed at the upper section with the flared bottom section comprised of a flange (210) that has a plurality of fastening holes (211) going through it and is coupled with the aforementioned fixed plate (100) to form chamber (a) and; fastening bolts (300) and fastening nuts (300') that fasten together with bolts the aforementioned fixed plate's (100) inner side with the outer side of the flange (210) on the bottom section of the aforementioned cylinder (200) to form chamber (a) and; a pressure gauge (400) coupled to the coupling pipe (226) of the pressure gauge coupling hole (224) that checks the pressure within chamber (a) in order to control the amount of inert gas that is injected and; opening/closing valves (500) connected to the injection pipes (110)(225) of the sample inlet (101) and the inert gas inlet (223) to open an close them and; a sample chamber (b) inside the aforementioned chamber (a) that stores the collected sample and creates and maintains constant pressure.

In addition, the method of use for the corrugated constant pressure cylinder having no micro leaks of the present invention is characterized by collecting a fixed amount of the sample in sample chamber (b) then closing the opening/closing valve (500), opening the opening/closing valve (500') of the inert gas inlet (223) on the cylinder (200) then gradually injecting inert gas through the inert gas inlet (223), making the corrugated cylinder (b10) of sample chamber (b) adjust in accordance with the increase in inert gas injected into the aforementioned chamber (a) until the internal pressure of chamber (a) and the internal pressure of sample chamber (b) reach equilibrium at a predetermined pressure, at which time the opening/closing valve (500') of the inert gas inlet (223) is closed.

EFFECTS OF THE INVENTION

According to the corrugated constant pressure cylinder having no micro leaks of the present invention as comprised above, a corrugated constant pressure cylinder having no micro leaks and its method of use is provided that removes the cause of gas leaks in the chamber and the sample chamber, allowing for the sample within the sample chamber to be maintained at a constant pressure to keep it in a liquid state during transport to the laboratory, which then allows it to be directly installed onto the analyzer to have the sample's composition be analyzed, resulting in reliable sample composition analysis results.

DESCRIPTION OF SUBPARTS 1 corrugated constant pressure cylinder apparatus having no micro leaks a chamber b sample chamber
b10 corrugated cylinder b20 end plate b21 end plate support fixture coupling groove b30 end plate support fixture b40 handle
100 fixed plate 101 sample inlet 102 o-ring groove 103 fastening holes 110 sample injection pipe 120 o-ring
200 cylinder 210 flange 211 fastening holes 220 closed side 221 support fixture insertion hole 222 o-ring groove 223 inert gas inlet 224 pressure gauge coupling hole 225 inert gas injection pipe 226 coupling pipe 230 o-ring
300 fastening bolts 300' fastening nuts
400 pressure gauge
500,500' opening/closing valve
600 traditional piston-type constant pressure cylinder 601 sample chamber 602 inert gas chamber 603 o-ring piston 604,604' opening/closing valve 605,605' connections The Preferred Embodiment for the Implementation of the Invention Hereafter, with references to the attached Figures, is a detailed explanation of the corrugated constant pressure cylinder having no micro leaks and its method of use of the present invention.

The terms or words used in these specifications and claims should not be limited to their normal or dictionary definitions, and based on the principle that the inventor can appropriately define the concept of a term in order to explain his invention in the best way possible, they must be interpreted as having definitions and concepts that are in accordance with the technical aspects of the present invention. As such, the embodiment set forth by this specification is merely one embodiment that is the most preferred and does not represent all of the technical aspects of the present invention, and as such it should be understood that there could be various equivalents and changes that can be made to these aspects when the present invention is applied. In addition, during this explanation of the present invention, if a detailed explanation of a related known function or composition is determined to unnecessarily obscure the substance of the present invention, then such detailed explanation will be omitted. Furthermore, while reference numbers are attached to each element of the composition, it should be noted that equivalent elements are, whenever possible, labeled with equivalent numbers and names, even though they may be displayed on different diagrams.

Figure 1:
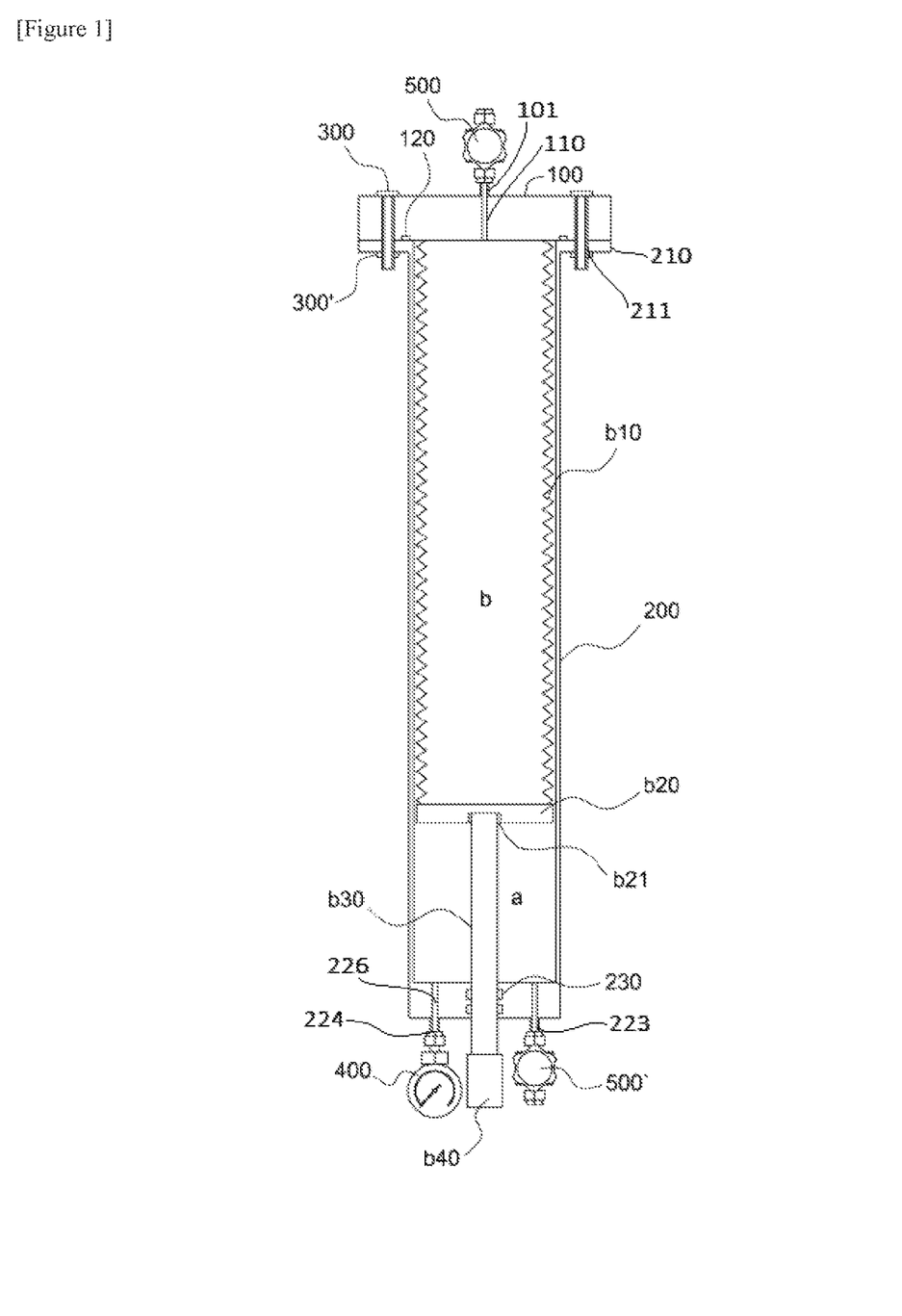
FIG. 1 is a cross-section diagram to explain the structure of the present invention's constant pressure cylinder apparatus that has no leaks.
Figure 2:
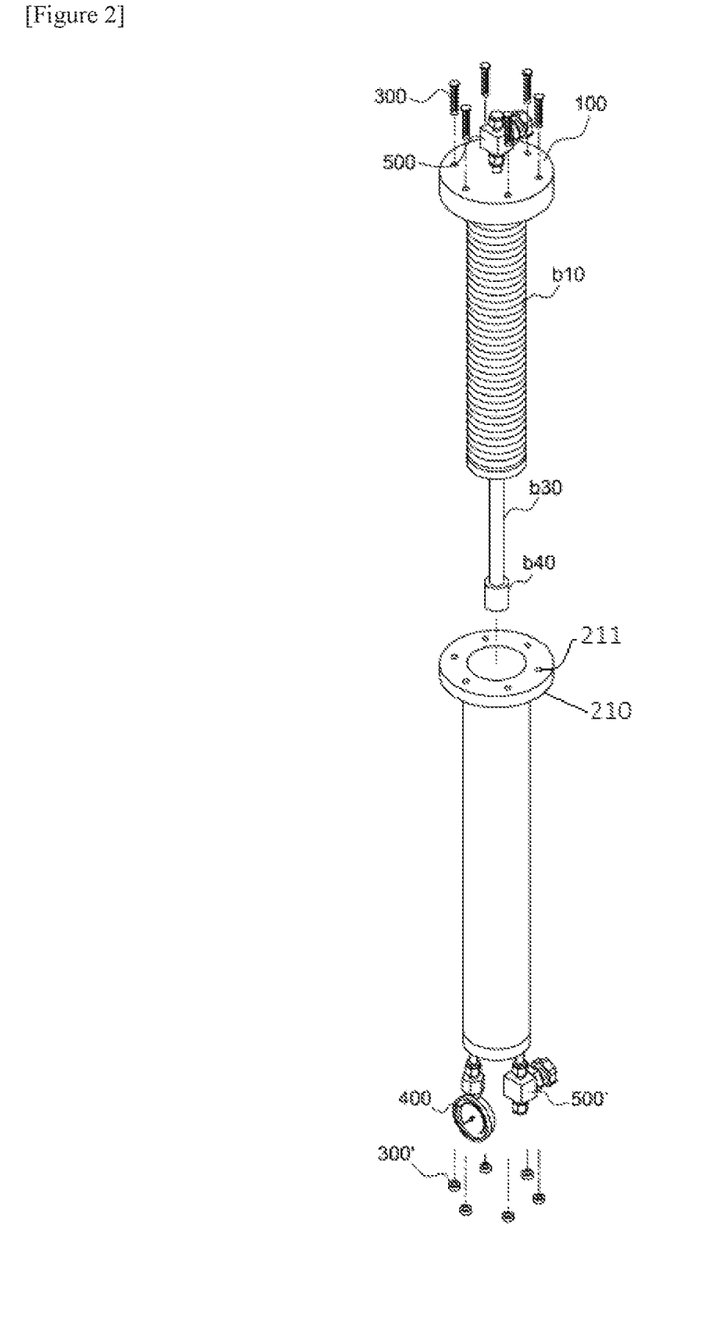
FIG. 2 is an exploded perspective diagram of FIG. 1.
Figure 3:
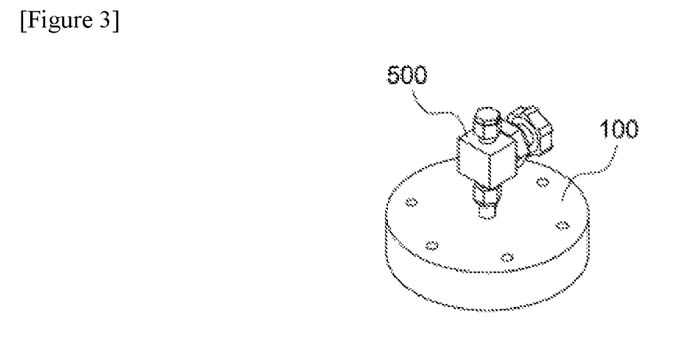
FIG. 3 is a top view perspective diagram to explain the fixed plate of the present invention.
Figure 4:
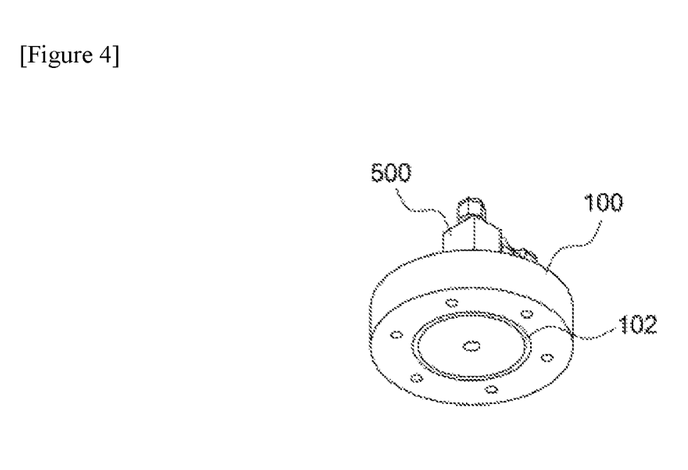
FIG. 4 is a bottom view perspective diagram of FIG. 3.
Figure 5:
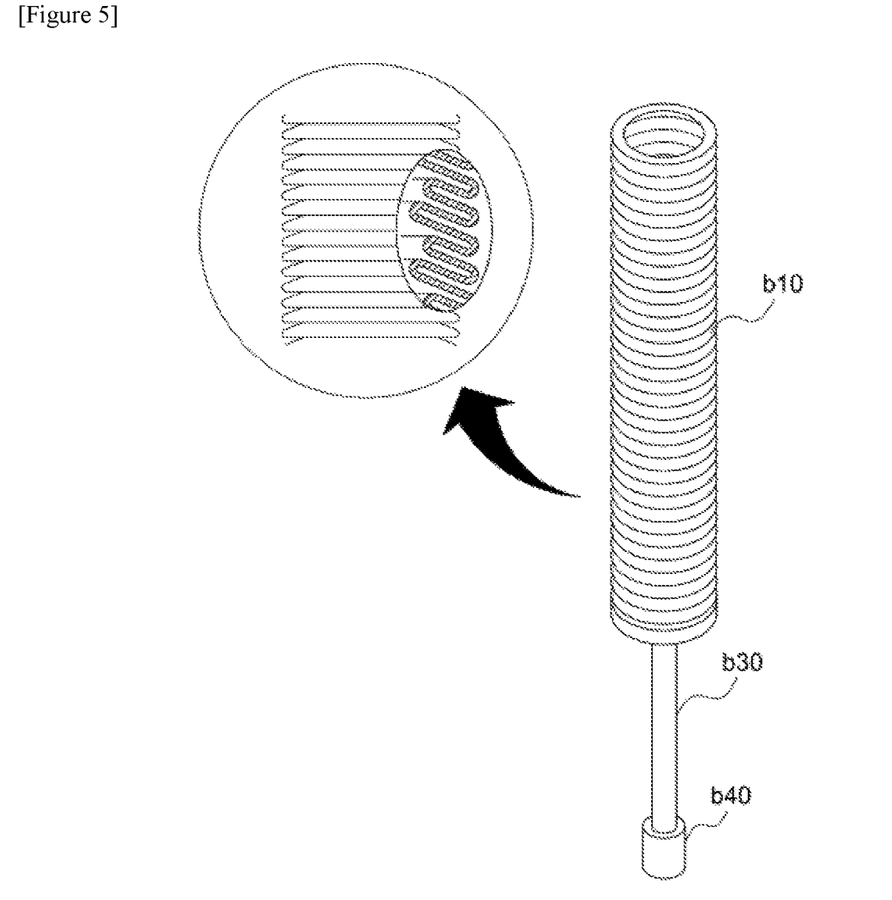
FIG. 5 is a diagram to explain the corrugations of the present invention.
Figure 6:
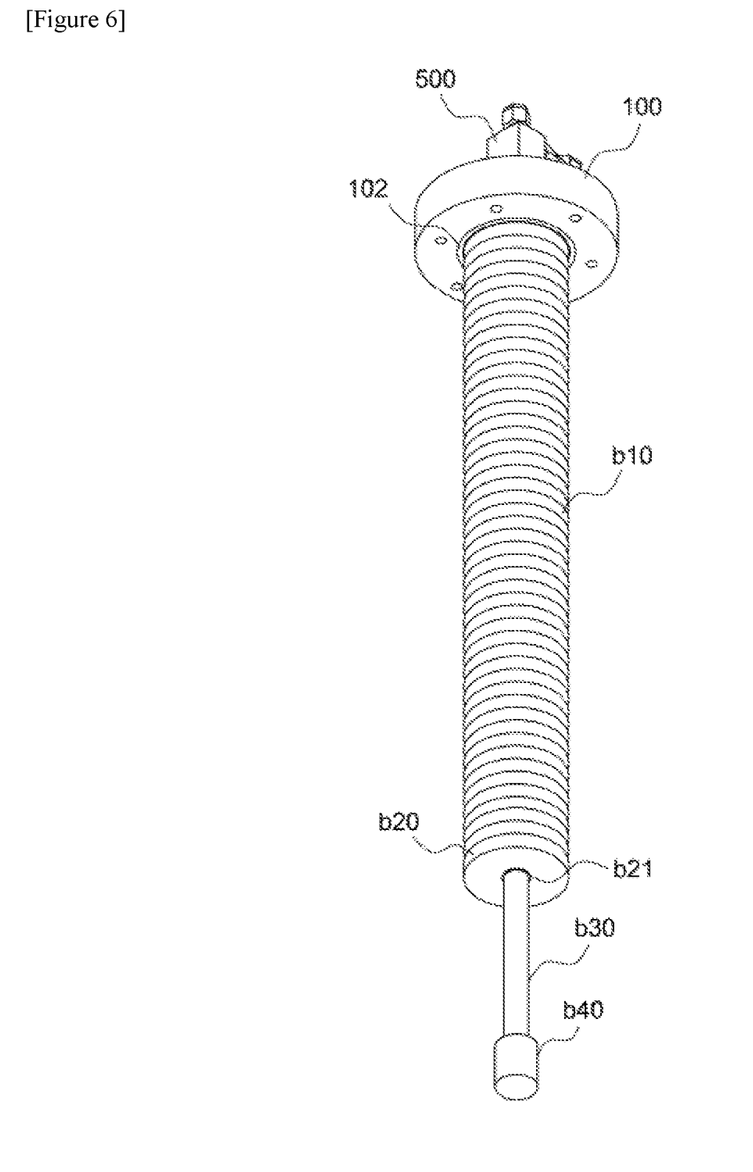
FIG. 6 is a diagram to explain chamber (a), which is formed by coupling the fixed plate with the corrugated cylinder.
Figure 7:
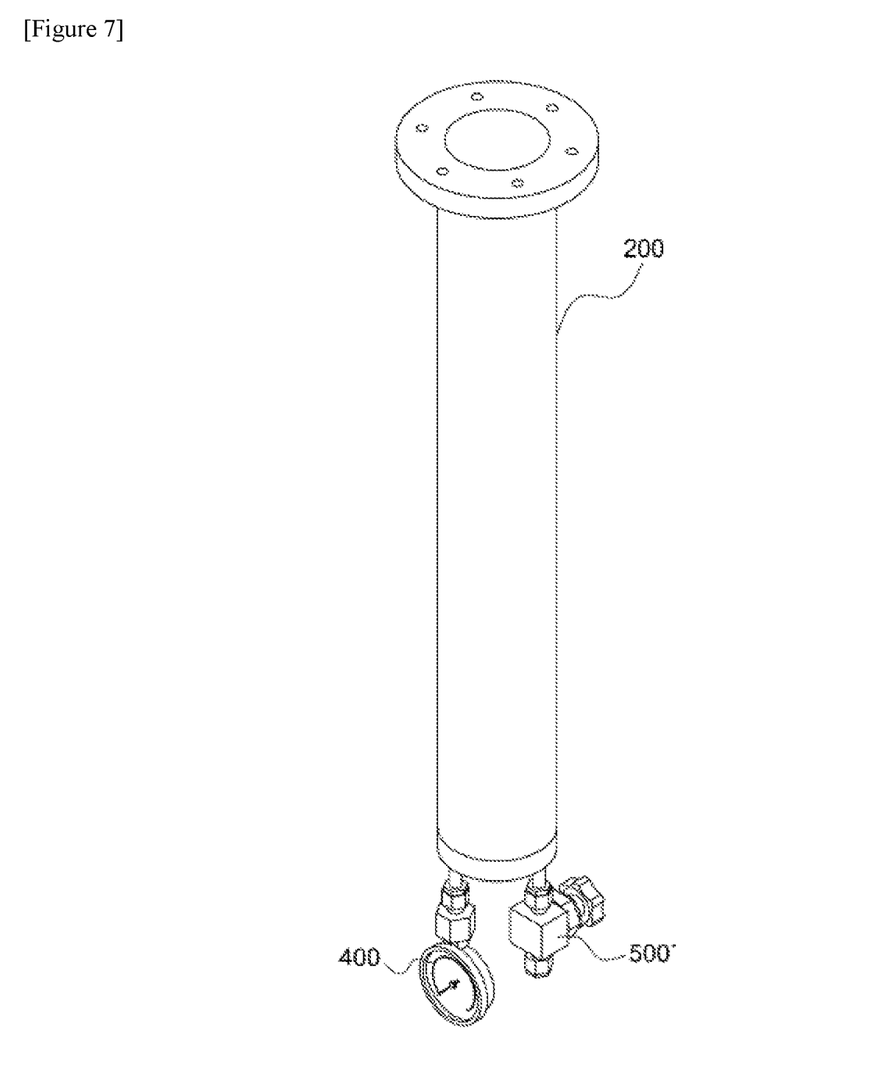
FIG. 7 is a perspective diagram to explain the present invention's constant pressure cylinder apparatus that has no leaks.
Figure 8:
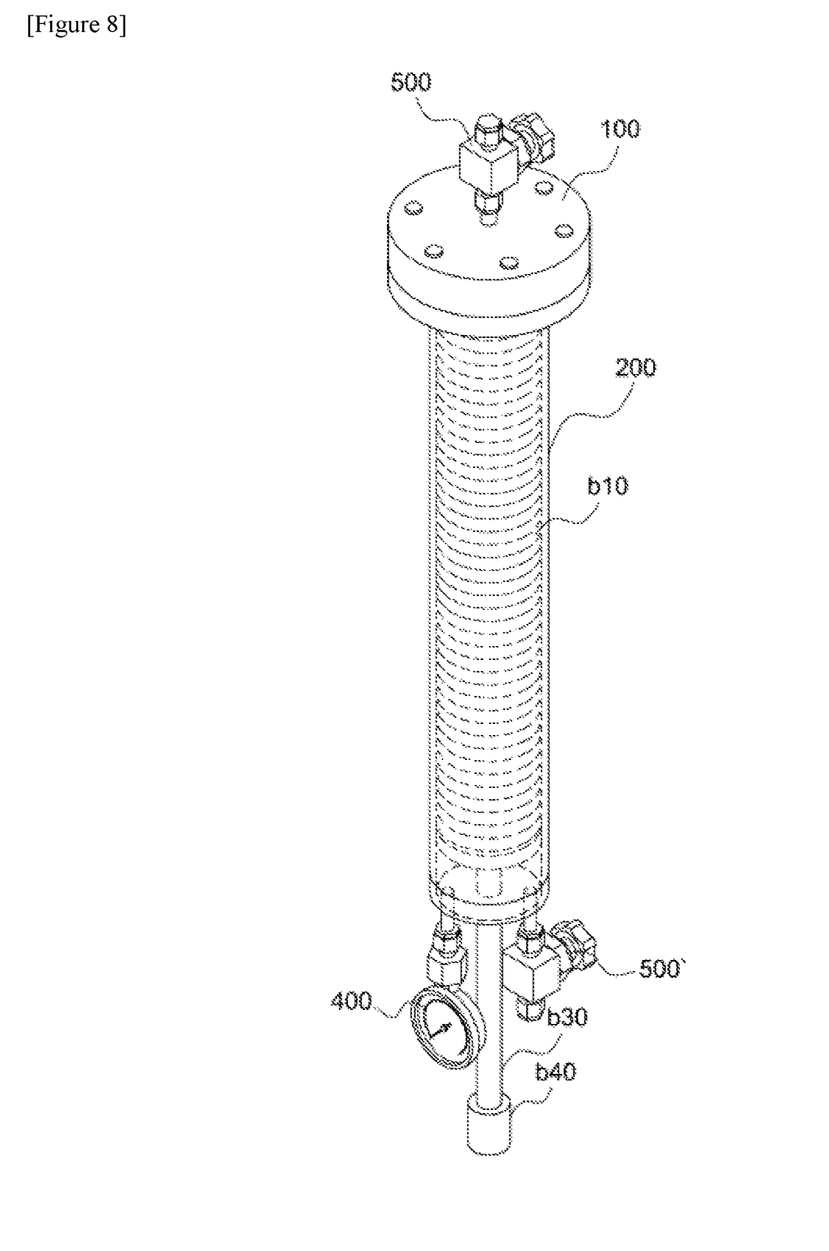
FIG. 8 is a diagram to explain the present invention's constant pressure cylinder apparatus that has no leaks.
Figure 9:
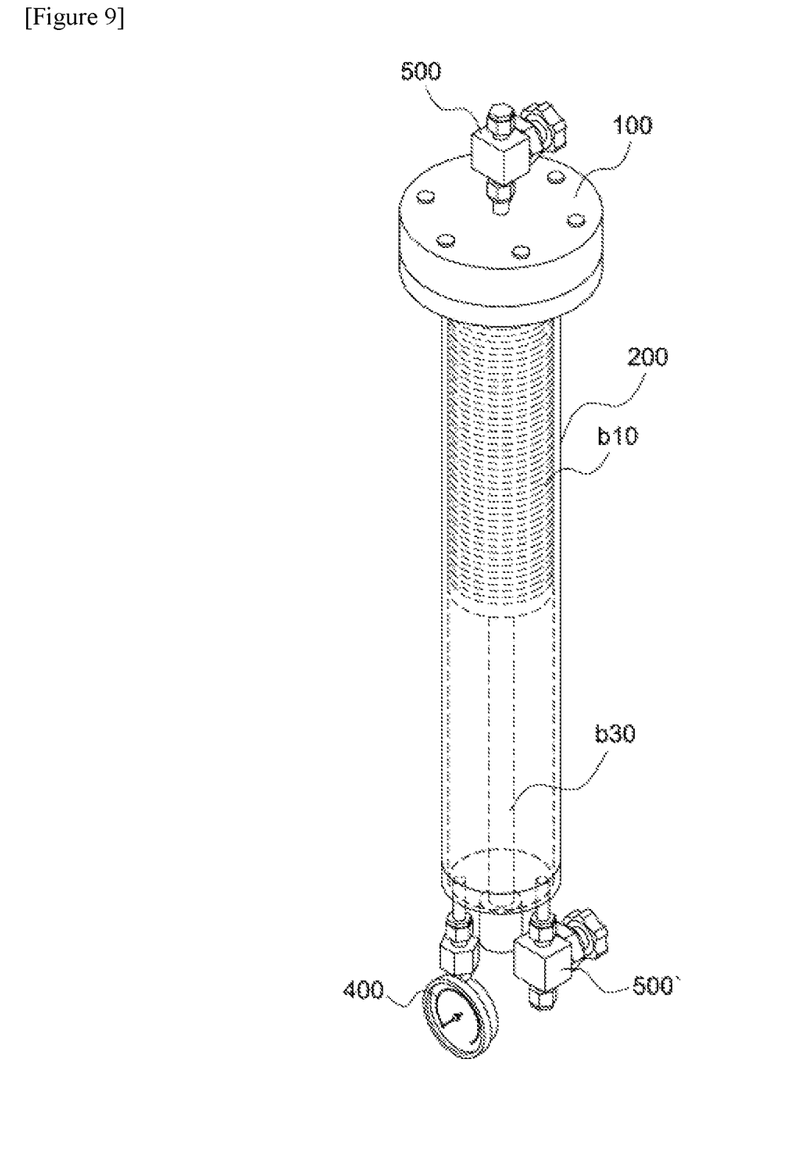
FIG. 9 is a diagram that shows the shrunken state of the corrugated cylinder.
Figure 10:
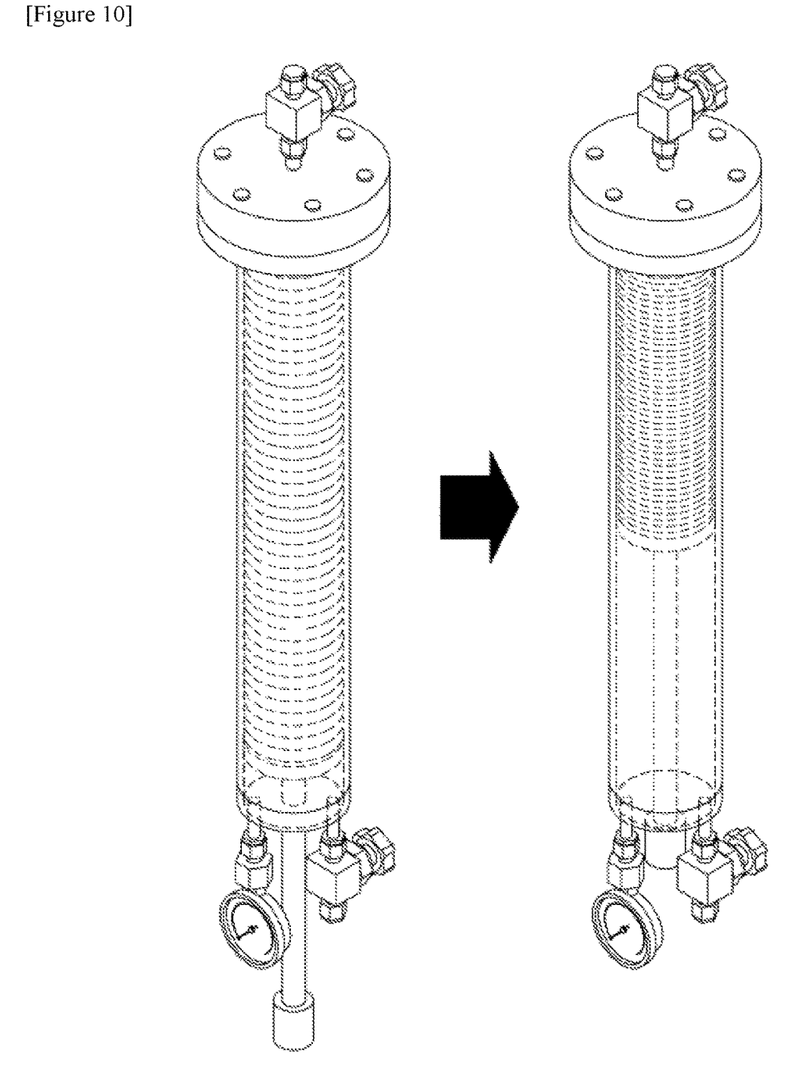
FIG. 10 is a diagram to explain the change in the corrugated cylinder after the injection of inert gas into chamber (a).

The attached FIG. 1 is a cross-section diagram to explain the structure of the corrugated constant pressure cylinder apparatus having no micro leaks of the present invention, FIG. 2 is an exploded diagram of FIG. 1, FIG. 3 is a top view perspective diagram to explain the fixed plate of the present invention, FIG. 4 is a bottom view perspective diagram of FIG. 3, FIG. 5 is a diagram to explain the corrugated cylinder of the present invention, FIG. 6 is a diagram to explain chamber (a) which is formed by coupling the fixed plate with the corrugated cylinder, FIG. 7 is a perspective diagram to explain the present invention's constant pressure cylinder apparatus that has no leaks, FIG. 8 is a diagram to explain the present invention's constant pressure cylinder apparatus that has no leaks, FIG. 9 is a diagram that shows the shrunken state of the corrugated cylinder, and FIG. 10 is a diagram to explain the change in the corrugated cylinder after the injection of inert gas into chamber (a).

As shown in the attached FIGS. 1 through 10, the corrugated constant pressure cylinder apparatus having no micro leaks (1) of the present invention is characterized by being comprised of a fixed plate (100) comprised of a circular steel plate with a fixed thickness that has a sample inlet (101) in the middle that goes through the plate, and is coupled with the bottom portion of a cylinder (200) to form chamber (a) and; a cylinder (200) comprised of a steel tube open at the bottom section and closed at the upper section with the flared bottom section comprised of a flange (210) that has a plurality of fastening holes (211) going through it and is coupled with the aforementioned fixed plate (100) to form chamber (a) and; fastening bolts (300) and fastening nuts (300') that fasten together with bolts the aforementioned fixed plate's (100) inner side with the outer side of the flange (210) on the bottom section of the aforementioned cylinder (200) to form chamber (a) and; a pressure gauge (400) coupled to the coupling pipe (226) of the pressure gauge coupling hole (224) that checks the pressure within chamber (a) in order to control the amount of inert gas that is injected and; opening/closing valves (500) connected to the sample inlet (101) and the inert gas inlet (223) and; a sample chamber (b) inside the aforementioned chamber (a) that stores the collected sample and creates and maintains constant pressure.

The following is a more detailed explanation.

The aforementioned fixed plate (100) is coupled to the cylinder (200) to form chamber (a), so as shown in FIG. 1 through FIG. 4, it is a circular steel plate of fixed thickness that has a sample inlet (101) that goes through the middle area, and on the aforementioned sample inlet (101) a sample injection pipe (110) is coupled and the outside of the sample injection pipe (110) has a opening/closing valve (500).

The inner side of the aforementioned fixed plate (100) has formed on it o-ring grooves (102), and on the aforementioned o-ring grooves (102) o-rings (120) are interposed so as to maintain the integrity of the seal.

A plurality of fastening holes (103) go through the aforementioned fixed plate (100) along its periphery.

The aforementioned cylinder (200) means a cylinder that is a hollow cylindrical device wherein a piston reciprocates as part of a steam engine or internal combustion engine.

The aforementioned cylinder (200), as shown in FIG. 1 through FIG. 7, is a steel tube that is open on the bottom and closed on the top, with the bottom being flared to form a flange (210), and the aforementioned flange (210) having a plurality of fastening holes (211) that go through it that align with the fastening holes (103) that go through the aforementioned fixed plate (100).

A support fixture insertion hole (221) goes through the top closed side (220) of the aforementioned cylinder (200), and as shown in FIG. 1, the inner side of the aforementioned through support fixture insertion hole (221) has formed on it two or more o-ring grooves (222), and o-rings (230) are interposed in these o-ring grooves (222).

On the outside of the aforementioned closed side (220) of the aforementioned cylinder (200) and radially around the aforementioned support fixture insertion hole (221) are the inert gas inlet (223) and the pressure gauge coupling hole (224) that each go through this surface, and an inert gas injection pipe (225) is coupled to the aforementioned inert gas inlet (223) and an opening/closing valve (500') is located on the outside of the aforementioned inert gas injection pipe (225).

The inside portion of the fixed plate (100) comes into contact with the outside of the flange (210) on the bottom of the aforementioned cylinder (200), and by fastening them together with the fastening bolts (300) and the fastening nuts (300'), as a whole they form chamber (a) as shown in FIG. 1.

In addition, a coupling pipe (226) is coupled to the aforementioned pressure gauge coupling hole (224), and a pressure gauge (400), which can detect the internal pressure of chamber (a), is attached to the aforementioned coupling pipe (226).

As the aforementioned pressure gauge (400) allows for checks of the internal pressure of chamber (a), the amount of inert gas injected can be controlled.

Sample chamber (b), which contains the sample and creates and maintains constant pressure, is located within the aforementioned cylinder (200).

As shown in FIG. 6, the aforementioned sample chamber (b) is comprised of a corrugated cylinder (b10) where one end is connected to the fixed plate (100) and the other end is connected to the end plate (b20) and; a circular end plate (b20) that is connected to the other end of the aforementioned corrugated cylinder (b10) and; an end plate support fixture (b30) that is coupled on one end to the outside of the aforementioned end plate (b20) and; a handle (b40) that is coupled to the other end of the aforementioned end plate support fixture (b30).

The aforementioned corrugated cylinder (b10) is an aluminum tube, and one end connects to the fixed plate (100).

It is preferable to form the aforementioned corrugated cylinder (b10) to have a length that is at least ½ and at most ⅔ the length of the cylinder (200).

Through trial and error, it was learned that if the length of the aforementioned corrugated cylinder (b10) was less than ½ the length of the cylinder (200), then the amount of the collected sample is small, resulting in less effective operation, and if the length was greater than ⅔ the length of the cylinder (200), then compression of the sample chamber (b) becomes difficult.

Furthermore, it is preferable to form a gap of 5-10 mm between the outer diameter of the aforementioned corrugated cylinder (b10) and the inner diameter of the cylinder (200).

Through trial and error, it was learned that if the gap between the outer diameter of the aforementioned corrugated cylinder (b10) and the inner diameter of the cylinder (200) was less than 5 mm, it would be inefficient as there was the possibility that the corrugated cylinder (b10) would come into contact with the inner surface of the cylinder (200), and if the gap between the outer diameter of the aforementioned corrugated cylinder (b10) and the inner diameter of the cylinder (200) was greater than 10 mm, it would be inefficient as there was the possibility that the aforementioned corrugated cylinder (b10) would collapse to one side.

The aforementioned end plate (b20) is formed of a circular aluminum plate that has a fixed thickness that is identical to the diameter of the aforementioned corrugated cylinder (b10), and is connected on one side to the other end of the aforementioned corrugated cylinder (b10).

The aforementioned corrugated cylinder (b10) is made of steel, so it is preferable to weld together the aforementioned fixed plate (100) and the aforementioned corrugated cylinder (b20) as it will prevent gas leaks.

An end plate support fixture coupling groove (b21) is formed in the center of the outside portion of the aforementioned end plate (b20), and one end of the end plate support fixture (b30) is coupled to the aforementioned end plate support fixture coupling groove (b21).

One end of the aforementioned end plate support fixture (b30) is coupled to the end plate support fixture coupling groove (b21) on the outside of the end plate (b20), and the other end goes through the support fixture insertion hole (221) located on the center of the closed side of the cylinder (200) to be exposed to the outside.

The aforementioned end plate support fixture (b30) is inserted to be movable as the o-rings (230) interposed at the support fixture insertion hole (221) in the center of the closed end of the aforementioned cylinder (200) maintain the integrity of the seal, while the other end protrudes from the outside of the cylinder's (200) closed side (220).

Depending on the intensity of the injection of inert gas, the aforementioned end plate support fixture (b30) allows for the prevention of the lateral movement of the corrugated cylinder (b10) by the pressure differential, allowing the equilibrium state of the corrugated cylinder (b10) to be maintained.

The other end of the end plate support fixture (b30) that protrudes out from the closed side (220) of the aforementioned cylinder (200) is coupled to a handle (b40) that also serves as a stopper for the end plate support fixture (b30).

The following is a detailed explanation of the method of usage for the present invention's corrugated constant pressure cylinder apparatus having no micro leaks.

As seen in FIG. 8, the present invention's corrugated constant pressure cylinder having no leaks (1) is completed by having the inside of the fixed plate (100), which is welded to one end of the corrugated cylinder (b10) of sample chamber (b), be connected to the outside of the cylinder's (200) flange (210) and be fastened in place by the fastening bolts (300) and the fastening nuts (300').

The corrugated constant pressure cylinder having no micro leaks (1) as composed above is transported to the sample collection site, where the sample injection pipe (110) is connected to the sample cylinder and the inert gas injection pipe (225) is connected to the inert gas cylinder.

The opening/closing valve (500) on the sample inlet (101) is opened and a predetermined amount of the sample is injected into sample chamber (b) through the sample inlet (101), after which the opening/closing valve (500) on the sample inlet (101) is closed.

Next, the opening/closing valve (600') on the inert gas inlet (223) is opened and inert gas is gradually injected through the inert gas inlet (223).

As shown in FIG. 10, the internal pressure of sample chamber (b) increases as the sample chamber (b) shrinks in accordance with increase in the amount of inert gas injected inside chamber (a). As the corrugated cylinder (b10) of sample chamber (b) adjusts in response, when the internal pressure of chamber (a) and the internal pressure of sample chamber (b) reach equilibrium, this pressure allows for the maintenance of an identical constant pressure.

In other words, when the internal pressure of chamber (a) increases in accordance with the increase in injected inert gas, the corrugated cylinder (b10) of sample chamber (b) is unable to withstand this pressure and shrinks, causing the internal pressure of sample chamber (b) to increase, and when the internal pressure of sample chamber (b) reaches equilibrium, the opening/closing valve (500') on the inert gas inlet (223) is closed.

The predetermined internal pressure of the aforementioned sample chamber (b) at which the injection of inert gas is halted means the point at which the sample inside sample chamber (b) is in liquid form.

At this point, inert gas is injected until the internal pressure of chamber (a) reaches the saturated vapor pressure of the hydrocarbon mixture sample as shown by the pressure gauge (400), and when the internal pressure of chamber (a) reaches the saturated vapor pressure of the hydrocarbon mixture sample then the internal pressure of chamber (a) and the internal pressure of sample chamber (b) reach equilibrium to become identical.

When the present invention's constant pressure cylinder apparatus that has no leaks (1) has collected the sample and formed and maintained a constant pressure as set forth above, if it is removed and transported to the laboratory to be directly installed onto the analyzer, then the liquid hydrocarbon mixture at a uniform pressure can be continuously injected, allowing for an increase in the reliability of the sample composition analysis.

In other words, the method of use for the corrugated constant pressure cylinder having no micro leaks of the present invention is characterized by collecting a fixed amount of the sample in sample chamber (b) then closing the opening/closing valve (500), opening the opening/closing valve (500') of the inert gas inlet (223) on the cylinder (200) then gradually injecting inert gas through the inert gas inlet (223), making the corrugated cylinder (b10) of sample chamber (b) adjust in accordance with the increase in inert gas injected into the aforementioned chamber (a) until the internal pressure of chamber (a) and the internal pressure of sample chamber (b) reach equilibrium at a predetermined pressure, at which time the opening/closing valve (500') of the inert gas inlet (223) is closed.

While the previous was a detailed explanation of the composition, operation, and effects of the preferred embodiment of the present invention's constant pressure cylinder apparatus that has no leaks with diagrams attached, the idea of the invention is not limited to this embodiment and can be implemented with many different alterations within the boundaries of the present invention's claims, the above detailed explanation of the present invention, and the attached diagrams, and it is exceedingly clear that such implementations would be within the scope of the present invention.

The invention claimed is:

1. A corrugated constant pressure cylinder apparatus having no micro leaks that is characterized by being comprised of a fixed plate (100) comprised of a circular steel plate with a fixed thickness that has a sample inlet (101) in the middle that goes through the plate, and is coupled with the bottom portion of a cylinder (200) to form chamber (a);

a cylinder (200) comprised of a steel tube open at the bottom section and closed at the upper section with the flared bottom section comprised of a flange (210) that has a plurality of fastening holes (211) going through it and is coupled with the aforementioned fixed plate (100) to form chamber (a);

fastening bolts (300) and fastening nuts (300') that fasten together with bolts the aforementioned fixed plate's (100) inner side with the outer side of the flange (210) on the bottom section of the aforementioned cylinder (200) to form chamber (a);

a pressure gauge (400) coupled to the coupling pipe (226) of the pressure gauge coupling hole (224) that checks the pressure within chamber (a) in order to control the amount of inert gas that is injected;

opening/closing valves (500) connected to the sample inlet (101) and an inert gas inlet (223); and a sample chamber (b) inside the aforementioned chamber (a) that stores the collected sample and creates and maintains constant pressure.

2. The corrugated constant pressure cylinder apparatus according to claim 1, wherein the aforementioned sample chamber (b) is characterized by being comprised of a corrugated cylinder (b10) where one end is connected to the fixed plate (100) and the other end is connected to the end plate (b20);

a circular end plate (b20) that is connected to the other end of the aforementioned corrugated cylinder (b10) and;

an end plate support fixture (b30) that is coupled on one end to the outside of the aforementioned end plate (b20); and a handle (b40) that is coupled to the other end of the aforementioned end plate support fixture (b30).

3. The corrugated constant pressure cylinder apparatus according to claim 2, wherein the aforementioned corrugated cylinder (b10) is characterized by having a length that is at least ½ and at most ⅔ the length of the cylinder (200).

4. The corrugated constant pressure cylinder apparatus according to claim 2, wherein the outer diameter of the aforementioned corrugated cylinder (b10) is characterized by forming a 5-10 mm gap with the inner diameter of the cylinder (200).

5. A method of use for a corrugated constant pressure cylinder apparatus having no micro leaks that is comprised of a fixed plate (100) comprised of a circular steel plate with a fixed thickness that has a sample inlet (101) in the middle that goes through the plate, and is coupled with the bottom portion of a cylinder (200) to form chamber (a);

a cylinder (200) comprised of a steel tube open at the bottom section and closed at the upper section with the flared bottom section comprised of a flange (210) that has a plurality of fastening holes (211) going through it and is coupled with the aforementioned fixed plate (100) to form chamber (a);

fastening bolts (300) and fastening nuts (300') that fasten together with bolts the aforementioned fixed plate's (100) inner side with the outer side of the flange (210) on the bottom section of the aforementioned cylinder (200) to form chamber (a);

a pressure gauge (400) coupled to the coupling pipe (226) of the pressure gauge coupling hole (224) that checks the pressure within chamber (a) in order to control the amount of inert gas that is injected and; opening/closing valves (500) connected to the sample inlet (101) and an inert gas inlet (223); and a sample chamber (b) inside the aforementioned chamber (a) that stores the collected sample and creates and maintains constant pressure, wherein the method of use for this corrugated constant pressure cylinder apparatus having no micro leaks is characterized by collecting a fixed amount of the sample in sample chamber (b) then closing the opening/closing valve (500), opening the opening/closing valve (500') of the inert gas inlet (223) on the cylinder (200) then gradually injecting inert gas through the inert gas inlet (223) to make the corrugated cylinder (b10) of sample chamber (b) adjust in accordance with the increase in inert gas injected into the aforementioned chamber (a) until the internal pressure of chamber (a) and the internal pressure of sample chamber (b) reach equilibrium at a predetermined pressure, at which time the opening/closing valve (500') of the inert gas inlet (223) is closed.

6. The method according to claim 5, having as a characteristic a predetermined pressure that is when the internal pressure of the aforementioned chamber (a) reaches equilibrium with the internal pressure of the aforementioned sample chamber (b), and the internal pressure of sample chamber (b) reaches the saturated vapor pressure.

\* \* \* \* \*